US011696736B2

(12) United States Patent
Kanakatte Gurumurthy et al.

(10) Patent No.: US 11,696,736 B2
(45) Date of Patent: Jul. 11, 2023

(54) ANATOMICAL LANDMARK DETECTION AND IDENTIFICATION FROM DIGITAL RADIOGRAPHY IMAGES CONTAINING SEVERE SKELETAL DEFORMATIONS

(71) Applicant: Tata Consultancy Services Limited, Mumbai (IN)

(72) Inventors: Aparna Kanakatte Gurumurthy, Bangalore (IN); Pavan Kumar Reddy Kancham, Bangalore (IN); Jayavardhana Rama Gubbi Lakshminarasimha, Bangalore (IN); Avik Ghose, Kolkata (IN); Murali Poduval, Mumbai (IN); Balamuralidhar Purushothaman, Bangalore (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 345 days.

(21) Appl. No.: 17/060,016

(22) Filed: Sep. 30, 2020

(65) Prior Publication Data
US 2021/0361249 A1    Nov. 25, 2021

(30) Foreign Application Priority Data
May 21, 2020    (IN) .............................. 202021021473

(51) Int. Cl.
*A61B 6/00*    (2006.01)
*G06N 3/08*    (2023.01)
(Continued)

(52) U.S. Cl.
CPC ............ *A61B 6/5258* (2013.01); *A61B 6/468* (2013.01); *A61B 6/527* (2013.01); *A61B 6/5211* (2013.01);
(Continued)

(58) Field of Classification Search
CPC ........... A61B 6/486; A61B 6/487; A61B 6/52; A61B 6/5205; A61B 6/5211;
(Continued)

(56) References Cited

U.S. PATENT DOCUMENTS 7,738,683 B2 * 6/2010 Cahill .................. G06T 7/0012
382/128
8,160,322 B2 * 4/2012 Dikmen ................... G06T 7/74
382/160
(Continued)

FOREIGN PATENT DOCUMENTS

EP    2 823 464 B1    10/2016

OTHER PUBLICATIONS

Torosdagli, Neslisah et al., "Deep Geodesic Learning for Segmentation and Anatomical Landmarking", Transactions on Medical Imaging, Oct. 2018, IEEE, https://arxiv.org/pdf/1810.04021.pdf.
(Continued)

*Primary Examiner* — Allen C. Ho
(74) *Attorney, Agent, or Firm* — Finnegan, Henderson, Farabow, Garrett & Dunner, LLP

(57) ABSTRACT

Conventionally, systems and methods have been provided for manual annotation of anatomical landmarks in digital radiography (DR) images. Embodiments of the present disclosure provides system and method for anatomical landmark detection and identification from DR images containing severe skeletal deformations. More specifically, motion artefacts and exposure are filtered from an input DR image to obtain a pre-processed DR image and probable/candidate anatomical landmarks comprised therein are identified. These probable candidate anatomical landmarks are assigned a score. A subset of the candidate anatomical landmarks (CALs) is selected as accurate anatomical landmarks based on comparison of the score with a pre-defined
(Continued)

threshold performed by a trained classifier. Position of remaining CALs may be fine-tuned for classification thereof as accurate anatomical landmarks or missing anatomical landmarks. The CALs may be further fed to the system for checking misalignment of any of the CALs and correcting the misaligned CALs.

20 Claims, 15 Drawing Sheets

(51) Int. Cl.
  *G06N 3/047* (2023.01)
  *G06T 7/00* (2017.01)
  *G06V 10/764* (2022.01)
  *G06V 10/82* (2022.01)
  *G06V 10/44* (2022.01)

(52) U.S. Cl.
  CPC .......... *A61B 6/5217* (2013.01); *A61B 6/5264* (2013.01); *G06N 3/047* (2023.01); *G06N 3/08* (2013.01); *G06T 7/0012* (2013.01); *G06V 10/454* (2022.01); *G06V 10/764* (2022.01); *G06V 10/82* (2022.01)

(58) Field of Classification Search
  CPC ... A61B 6/5217; A61B 6/5258; A61B 6/5264; A61B 6/527; A61B 6/50; A61B 6/501; A61B 6/502; A61B 6/503; A61B 6/504; A61B 6/505; A61B 6/506; A61B 6/507; A61B 6/5282; A61B 6/5294
  USPC .................... 382/131, 132; 378/62, 162, 165
  See application file for complete search history.

(56) References Cited

U.S. PATENT DOCUMENTS

| | | | | |
|---|---|---|---|---|
| 8,160,341 B2* | 4/2012 | Peng | ........................ | G06T 7/73 382/128 |
| 8,958,614 B2* | 2/2015 | Zhan | ........................ | G06T 7/73 382/128 |
| 9,122,959 B2* | 9/2015 | Zhou | ........................ | G06T 7/149 |
| 9,218,542 B2* | 12/2015 | Zhan | ........................ | G06T 19/00 |
| 9,336,457 B2* | 5/2016 | Raykar | ........................ | G06T 7/33 |
| 9,740,710 B2* | 8/2017 | Han | ........................ | G06T 7/10 |
| 9,984,283 B2* | 5/2018 | Davatzikos | ........................ | G06V 10/764 |
| 10,049,457 B2* | 8/2018 | Abraham | ........................ | G06F 18/24323 |
| 10,210,613 B2* | 2/2019 | Xu | ........................ | A61B 5/4887 |
| 10,521,911 B2* | 12/2019 | Odry | ........................ | G06T 7/0016 |
| 10,568,600 B2* | 2/2020 | Guntzer | ........................ | G06T 7/0014 |
| 10,825,168 B2* | 11/2020 | Tegzes | ........................ | G06T 7/11 |
| 10,878,219 B2* | 12/2020 | Zhou | ........................ | G06N 3/045 |
| 10,878,569 B2* | 12/2020 | Akselrod-Ballin | ........................ | G06V 10/764 |
| 11,158,069 B2* | 10/2021 | Shi | ........................ | G06T 7/30 |
| 11,227,683 B2* | 1/2022 | Morard | ........................ | G06T 7/0014 |
| 11,403,750 B2* | 8/2022 | Kamen | ........................ | G06V 10/454 |

OTHER PUBLICATIONS

Han, Dong et al., "Robust Anatomical Landmark Detection with Application to MR Brain Image Registration", Computerized Medical Imaging and Graphics, Dec. 2015, vol. 46, Part 3 pp. 277-290, Sciencedirect, https://webpages.uncc.edu/~szhang16/paper/ISBI15_knee.pdf.

Zhangy, Jun et al., "Detecting Anatomical Landmarks from Limited Medical Imaging Data using Two-Stage Task-Oriented Deep Neural Networks", Transactions on Image Processing, Jun. 2017, pp. 4753-4764, IEEE, https://www.researchgate.net/publication/317988506_Detecting_Anatomical_Landmarks_From_Limited_Medical_Imaging_Data_Using_Two-Stage_Task-Oriented_Deep_Neural_Networks/link/5aad1acb458515ecebe7cb30/download.

Wang, Song et al., "Shape Deformation: SVM Regression and Application to Medical Image Segmentation", International Conference on Computer Vision. ICCV 2001, Jul. 2001, IEEE https://www.researchgate.net/publication/3906129_Shape_deformation_SVM_Regression_and_application_to_medical_image_segmentation/link/004635278ff0ddc7f7000000/download.

\* cited by examiner

ANATOMICAL LANDMARK DETECTION AND IDENTIFICATION FROM DIGITAL RADIOGRAPHY IMAGES CONTAINING SEVERE SKELETAL DEFORMATIONS

PRIORITY CLAIM

This U.S. patent application claims priority under 35 U.S.C. § 119 to: India Application No. 202021021473, filed on May 21, 2020. The entire contents of the aforementioned application are incorporated herein by reference.

TECHNICAL FIELD

The disclosure herein generally relates to medical imaging techniques, and, more particularly, to anatomical landmark detection and identification from digital radiography images containing severe skeletal deformations.

BACKGROUND

Digital Radiography (DR) is a method of radiograph where digital sensors are used instead of traditional photographic film to output DR images. These DR images can be stored and digitally processed to enhance the readability. As a result, the inaccurate dosage in incident beam manifests in the form of noise and artifacts (or artefacts and may be interchangeably used herein) rather than dark or bright images as in the case of films. Higher dose produces high quality images but at the higher health risks for the patient. Accurate detection of anatomical landmark is a key step in medical image analysis and surgical planning. Anatomical landmarks are biologically meaningful locations of an organism, that have high inter-subject consistency. These include external landmarks, as well as internal landmarks on data acquired through modalities such as ultrasound, X-Ray, Computed tomography (CT), Magnetic resonance imaging (MRI), etc. Landmark detection on DR images is challenging since the local information around the landmarks may be very less due to the projection of three-dimensional human body into a two-dimensional image. Also, presence of any artifacts makes it even a harder problem. Most common artifacts observed in radiography is motion artifacts. During the data acquisition process motion effects induced by respiration, cardiac motion and patient restlessness produce artifacts that manifest as blurring, doubling and distortion in the reconstructed images which may lead to inaccurate diagnosis. Though care is taken to minimize such artifacts, there are certain conditions under which it is not possible to avoid motion. In any case, a repeat of the imaging process puts the patient at higher risk.

Another artifact observed is the exposure factor due to technical issues which provides over or underexposed images. It is very difficult to detect landmarks in either of these cases, even to an expert. Traditionally, anatomical landmarks are identified manually by an expert during treatment planning. This process is exhaustive, time consuming and subjective, leading to observer errors.

Apart from the difficulties in detecting landmarks due to imaging artefacts, another scenario where the detection becomes very hard is in the presence of deformations/abnormalities in the patient. In some extreme cases, the landmarks might be entirely missing because of underlying pathological conditions. Most of the existing methods are designed to detect the landmarks under the assumption of normal cases. And in many cases, they derive the information from standard atlas models for detection. However, these models cannot be adapted directly for abnormal cases.

SUMMARY

Embodiments of the present disclosure present technological improvements as solutions to one or more of the above-mentioned technical problems recognized by the inventors in conventional systems. For example, in one aspect, there is provided a processor implemented method for detecting anatomical landmarks in abnormal subjects. The method comprises: obtaining, via one or more hardware processors, one or more digital radiography (DR) images of an abnormal subject, wherein the one or more DR images comprise one or more deformed structures of the abnormal subject, and wherein the one or more deformed structures are representative of one or more abnormalities observed in the abnormal subject; filtering, using a first trained neural network executed by the one or more hardware processors, one or more artifacts from the obtained one or more DR images to obtain a pre-processed DR image comprising the one or more deformed structures of the abnormal subject; generating, using a second trained neural network, a heat map based on the pre-processed DR image, wherein the heat map comprises one or more locations of corresponding one or more probable anatomical landmarks identified in the pre-processed DR image; generating, by a trained classifier executed by the one or more hardware processors, a first probability score for each of the one or more patches indicative of the one or more locations of the corresponding one or more probable anatomical landmarks; performing a first comparison of the first probability score of each of the one or more patches with a pre-defined threshold; and selecting, based on the first comparison, a subset of probable anatomical landmarks serving as a set of detected anatomical landmarks.

In one embodiment, each detected anatomical landmark from the set of detected anatomical landmarks has the first probability score higher than the pre-defined threshold.

In an embodiment, when the first probability score of remaining subset of probable anatomical landmarks from the one or more probable anatomical landmarks is less than the pre-defined threshold, the method comprises: fine-tuning the remaining subset of probable anatomical landmarks from the one or more probable anatomical landmarks, using an anatomical atlas comprised in a memory to obtain a set of fine-tuned probable anatomical landmarks; or identifying the remaining subset of probable anatomical landmarks from the one or more probable anatomical landmarks as one or more missing anatomical landmarks.

In an embodiment, the method further comprises generating, by the trained classifier, a second probability score for the set of fine-tuned probable anatomical landmarks; performing a second comparison of the second probability score of each fine-tuned probable anatomical landmark from the set of fine-tuned probable anatomical landmarks with the pre-defined threshold; and selecting, based on the second comparison, a subset of probable anatomical landmarks serving as another set of detected anatomical landmarks.

In an embodiment, the method further comprises identifying remaining fine-tuned probable anatomical landmarks from the set of fine-tuned probable anatomical landmarks as one or more missing anatomical landmarks, wherein each of the one or more identified missing anatomical landmarks has the second probability score less than the pre-defined threshold.

In an embodiment, the step of filtering one or more artifacts from the obtained one or more DR images to obtain a pre-processed DR image comprises: applying, by the first trained neural network, (i) the domain knowledge and (ii) motion details of the abnormal subject on the obtained one or more DR images, wherein the motion details during an exposure are captured through at least one of (i) one or more sensors attached to the abnormal subject and (ii) an external image capturing device; estimating a noise level in the obtained one or more DR images; applying one or more network weights of the first trained neural network to the obtained one or more DR images based on the estimated noise level; and obtaining the pre-processed DR image that is (i) free from one or more errors in the one or more artifacts and (ii) free from under exposure, (iii) free from over exposure, or (iv) combinations thereof.

In an embodiment, the method further comprises determining one or more misaligned anatomical landmarks from the one or more probable anatomical landmarks; realigning, by using a three-dimensional (3D) based two-dimensional (2D) deformable model, the one or more misaligned anatomical landmarks to a desired position by using at least one of an anatomical atlas and an associated domain knowledge comprised in a memory, to obtain one or more realigned anatomical landmarks; and identifying the one or more realigned anatomical landmarks as at least one of a set of accurate anatomical landmarks and a set of missing anatomical landmarks.

In another aspect, there is provided a system for detecting anatomical landmarks in abnormal subjects. The system comprises: a memory storing instructions; one or more communication interfaces; and one or more hardware processors coupled to the memory via the one or more communication interfaces, wherein the one or more hardware processors are configured by the instructions to: obtain one or more digital radiography (DR) images of an abnormal subject, wherein the one or more DR images comprise one or more deformed structures of the abnormal subject, and wherein the one or more deformed structures are representative of one or more abnormalities observed in the abnormal subject; filter, using a first trained neural network executed by the one or more hardware processors, one or more artifacts from the obtained one or more DR images to obtain a pre-processed DR image comprising the one or more deformed structures of the abnormal subject; generate, using a second trained neural network, a heat map based on the pre-processed DR image, wherein the heat map comprises one or more locations of corresponding one or more probable anatomical landmarks identified in the pre-processed DR image; generate, by a trained classifier executed by the one or more hardware processors, a first probability score for each of the one or more patches indicative of the one or more locations of the corresponding one or more probable anatomical landmarks; perform a first comparison of the first probability score of each of the one or more patches with a pre-defined threshold; and select, based on the first comparison, a subset of probable anatomical landmarks serving as a set of detected anatomical landmarks.

In one embodiment, each detected anatomical landmark from the set of detected anatomical landmarks has the first probability score higher than the pre-defined threshold.

In an embodiment, when the first probability score of remaining subset of probable anatomical landmarks from the one or more probable anatomical landmarks is less than the pre-defined threshold, the one or more hardware processors are further configured to: fine-tune the remaining subset of probable anatomical landmarks from the one or more probable anatomical landmarks, using an anatomical atlas comprised in the memory to obtain a set of fine-tuned probable anatomical landmarks; or identify the remaining subset of probable anatomical landmarks from the one or more probable anatomical landmarks as one or more missing anatomical landmarks.

In an embodiment, the one or more hardware processors are further configured to generate, via the trained classifier, a second probability score for the set of fine-tuned probable anatomical landmarks; perform a second comparison of the second probability score of each fine-tuned probable anatomical landmark from the set of fine-tuned probable anatomical landmarks with the pre-defined threshold; and select, based on the second comparison, a subset of probable anatomical landmarks serving as another set of detected anatomical landmarks.

In an embodiment, the one or more hardware processors are further configured to identify remaining fine-tuned probable anatomical landmarks from the set of fine-tuned probable anatomical landmarks as one or more missing anatomical landmarks, wherein each of the one or more identified missing anatomical landmarks has the second probability score less than the pre-defined threshold.

In an embodiment, the one or more artifacts from the obtained one or more DR images are filtered to obtain the pre-processed DR image by: applying, by the first trained neural network, (i) the domain knowledge and (ii) motion details of the abnormal subject on the obtained one or more DR images, wherein the motion details during an exposure are captured through at least one of (i) one or more sensors attached to the abnormal subject and (ii) an external image capturing device; estimating a noise level in the obtained one or more DR images; applying one or more network weights of the first trained neural network to the obtained one or more DR images based on the estimated noise level; and obtaining the pre-processed DR image that is (i) free from one or more errors in the one or more artifacts and (ii) free from under exposure, (iii) free from over exposure, or (iv) combinations thereof.

In an embodiment, the one or more hardware processors are further configured to determine one or more misaligned anatomical landmarks from the one or more probable anatomical landmarks; realign, by using a three-dimensional (3D) based two-dimensional (2D) deformable model, the one or more misaligned anatomical landmarks to a desired position by using at least one of an anatomical atlas and an associated domain knowledge comprised in the memory, to obtain one or more realigned anatomical landmarks; and identify the one or more realigned anatomical landmarks as at least one of a set of accurate anatomical landmarks and a set of missing anatomical landmarks.

In yet another embodiment, there is provided a computer program product comprising a non-transitory computer readable medium having a computer readable program embodied therein, wherein the computer readable program, when executed on a computing device, causes the computing device to detect anatomical landmarks in abnormal subjects by: obtaining, via one or more hardware processors of the computing device, one or more digital radiography (DR) images of an abnormal subject, wherein the one or more DR images comprise one or more deformed structures of the abnormal subject, and wherein the one or more deformed structures are representative of one or more abnormalities observed in the abnormal subject; filtering, using a first trained neural network executed by the one or more hardware processors, one or more artifacts from the obtained one or more DR images to obtain a pre-processed DR image comprising the one or more deformed structures of the abnormal subject; generating, using a second trained neural network executed the one or more hardware processors, a heat map based on the pre-processed DR image, wherein the heat map comprises one or more locations of corresponding one or more probable anatomical landmarks identified in the pre-processed DR image; generating, by a trained classifier executed by the one or more hardware processors, a first probability score for each of the one or more patches indicative of the one or more locations of the corresponding one or more probable anatomical landmarks; performing a first comparison of the first probability score of each of the one or more patches with a pre-defined threshold; and selecting, based on the first comparison, a subset of probable anatomical landmarks serving as a set of detected anatomical landmarks.

In one embodiment, each detected anatomical landmark from the set of detected anatomical landmarks has the first probability score higher than the pre-defined threshold.

In an embodiment, when the first probability score of remaining subset of probable anatomical landmarks from the one or more probable anatomical landmarks is less than the pre-defined threshold, the method comprises: fine-tuning the remaining subset of probable anatomical landmarks from the one or more probable anatomical landmarks, using an anatomical atlas comprised in a memory to obtain a set of fine-tuned probable anatomical landmarks; or identifying the remaining subset of probable anatomical landmarks from the one or more probable anatomical landmarks as one or more missing anatomical landmarks.

In an embodiment, the computer readable program, when executed on the computing device, further causes the computing device to generate, by using the trained classifier, a second probability score for the set of fine-tuned probable anatomical landmarks; perform a second comparison of the second probability score of each fine-tuned probable anatomical landmark from the set of fine-tuned probable anatomical landmarks with the pre-defined threshold; and select, based on the second comparison, a subset of probable anatomical landmarks serving as another set of detected anatomical landmarks.

In an embodiment, the computer readable program, when executed on the computing device, further causes the computing device to identify remaining fine-tuned probable anatomical landmarks from the set of fine-tuned probable anatomical landmarks as one or more missing anatomical landmarks, wherein each of the one or more identified missing anatomical landmarks has the second probability score less than the pre-defined threshold.

In an embodiment, the one or more artifacts from the obtained one or more DR images are filtered to obtain the pre-processed DR image comprises: applying, by the first trained neural network, (i) the domain knowledge and (ii) motion details of the abnormal subject on the obtained one or more DR images, wherein the motion details during an exposure are captured through at least one of (i) one or more sensors attached to the abnormal subject and (ii) an external image capturing device; estimating a noise level in the obtained one or more DR images; applying one or more network weights of the first trained neural network to the obtained one or more DR images based on the estimated noise level; and obtaining the pre-processed DR image that is (i) free from one or more errors in the one or more artifacts and (ii) free from under exposure, (iii) free from over exposure, or (iv) combinations thereof.

In an embodiment, one or more misaligned anatomical landmarks are determined in the one or more probable anatomical landmarks wherein the one or more misaligned anatomical landmarks are realigned from a current position to a desired position by a three-dimensional (3D) based two-dimensional (2D) deformable model by using at least one of an anatomical atlas and an associated domain knowledge comprised in a memory, to obtain one or more realigned anatomical landmarks. The one or more realigned anatomical landmarks are identified as at least one of a set of accurate anatomical landmarks and a set of missing anatomical landmarks.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
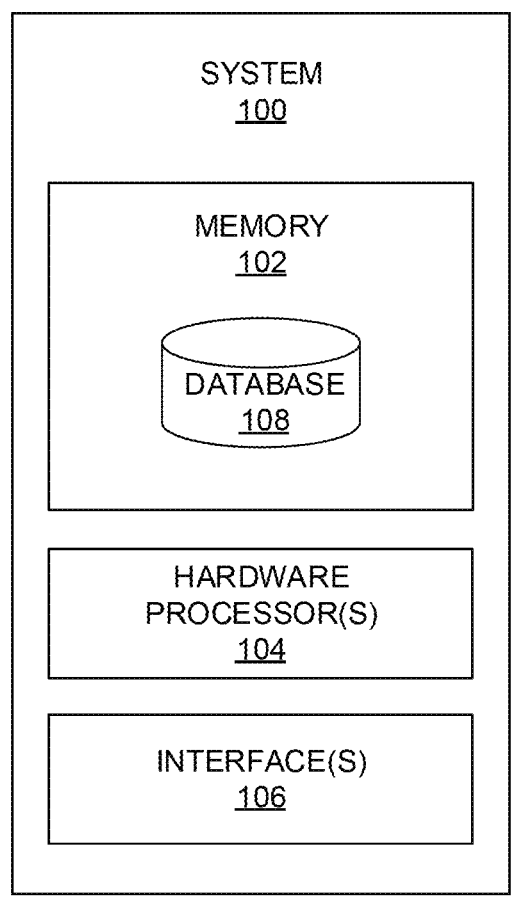
FIG. 1 depicts a system for anatomical landmark detection and identification from digital radiography images containing severe skeletal deformations, in accordance with an embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

2-D X-rays are the mainstay of skeletal imaging and diagnosis and are obtained in at least two planes. The rationale is that two or more views enable a clinician to visualize three dimensionally from a 2-D image to diagnose as well as plan surgeries. The process of reading a skeletal radiograph involves identification of landmarks (also referred as anatomical landmarks and interchangeably used herein) and their relationship to each other before looking for normal and abnormal, these landmarks are a valuable source of information to the disease condition and diagnosis. For example, from position and visualization of the lesser trochanter it can be inferred that at what position the limb is lying. Landmarks also form basis of making angular and linear measurements in the diagnostic as well as surgical planning process.

Identification of such landmarks is a first step in surgical planning and templating for surgery. Templating is a process wherein a pre-existing implant is superimposed on the radiograph to determine best fit and size and for this to be done, certain landmarks need to be identified as guiding the template position to most closely replicate the native bone. For example, in the acetabulum, teardrop marks an inferiormost extent of the acetabulum and the place where the lower edge of the implanted component must lie. The teardrop becomes the guide to the depth of placing the component also.

In scoliosis, the spine not only tilts laterally but also rotate along a vertical axis and some anteroposterior deformity may also exist (kyphoscoliosis). This makes identifying the exact anatomy very difficult on AP and lateral x-rays as well as on improperly executed Computed Tomography (CT) scans. The surgeon required to put pedicle screws at designated levels in many of these vertebrae must de-rotate and correct the deformity. Identifying the landmarks in such deformed conditions would help in pre-operatively understanding and planning screw trajectory, thus taking off much of the effort needed in surgery as well as enhancing safety and accuracy. Radiographs can appear in different distorting landmarks when the limb is deformed, for example, a fixed flexion deformity of the hip or degenerative scoliosis of the lumbar spine. These can also be obscured in arthritis and destructive pathology as well as in congenital and developmental conditions where they can be absent altogether. It is therefore of utmost important that accurate anatomical landmarks are detected to help with diagnostics and as well as surgical planning process. Examples of Scoliosis and Cephalometric discussed by the present disclosure as use cases are way of one or more instances of how the method and system of the present disclosure can be used/implemented in medical imaging and analysis for understanding a deformed skeletal image and planning a surgical procedure, and such examples shall not be construed as limiting the scope of present disclosure. In other words, other instances such as detecting a vertebral fracture and other bone fractures, planning hip and knee replacements and trauma surgery can also be realized in practice by system and method of the present disclosure described herein. Therein both diagnostic and therapeutic implications exist.

Referring now to the drawings, and more particularly to FIGS. 1 through 11B, where similar reference characters denote corresponding features consistently throughout the figures, there are shown preferred embodiments and these embodiments are described in the context of the following exemplary system and/or method.

FIG. 1 depicts a system 100 for anatomical landmark detection and identification from digital radiography images containing severe skeletal deformations, in accordance with an embodiment of the present disclosure. In an embodiment, the system 100 includes one or more hardware processors 104, communication interface device(s) or input/output (I/O) interface(s) 106 (also referred as interface(s)), and one or more data storage devices or memory 102 operatively coupled to the one or more hardware processors 104. The one or more processors 104 may be one or more software processing components and/or hardware processors. In an embodiment, the hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is/are configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, a database 108 is comprised in the memory 102, wherein the database 108 comprises digital radiography (DR) images of abnormal subject(s), the DR images containing severe skeletal deformations.

The information stored in the database 108 may further comprise details on pre-processed DR images, for example, details include information on filtering motion artifacts from the DR images, or filtering noise present in the DR images and the like. The database 108 further comprises a pre-generated deformable model that is trained on a set of DR images to output simulated DR image(s) for each condition (e.g., severe deformation condition) associated with abnormal subject(s). Furthermore, the database 108 comprises information pertaining to candidate anatomical landmark(s) (also referred as probable anatomical landmark(s) and may be interchangeably used herein), wherein the candidate anatomical landmark(s) (CALs) are fed to a trained classifier that classifies the candidate anatomical landmark(s) (CALs) as one of an accurate anatomical landmark(s) AAL or a missing anatomical landmark(s) (MAL). A score is associated with each of the candidate anatomical landmark, wherein the score is stored in the database 102 for further processing and analysis. The memory 102 further stores a pre-defined threshold, wherein the pre-defined threshold is used for comparison with the score of the candidate anatomical landmark(s) (CALs) for classification thereof.

In an embodiment, one or more artificial intelligence techniques, one or more classifiers, one or more machine learning models, one or more neural network(s) and the like, as known in the art are comprised in the memory 102 and invoked as per the requirement to perform the methodologies described herein. In an embodiment, prior to invoking one of more of the one or more artificial intelligence techniques, the one or more classifiers, the one or more machine learning models, the one or more neural network(s) these the one or more artificial intelligence techniques, the one or more classifiers, the one or more machine learning models, the one or more neural network(s) are trained using training dataset (e.g., volume of DR images such as computed topography images, pre-processed DR images, deformable models, candidate anatomical landmarks, accurate anatomical landmarks, missing anatomical landmarks, realigned anatomical landmarks, and the like). The memory 102 further comprises (or may further comprise) information pertaining to input(s)/output(s) of each step performed by the systems and methods of the present disclosure. In other words, input(s) fed at each step and output(s) generated at each step are comprised in the memory 102 and can be utilized in further processing and analysis.

Figure 2:
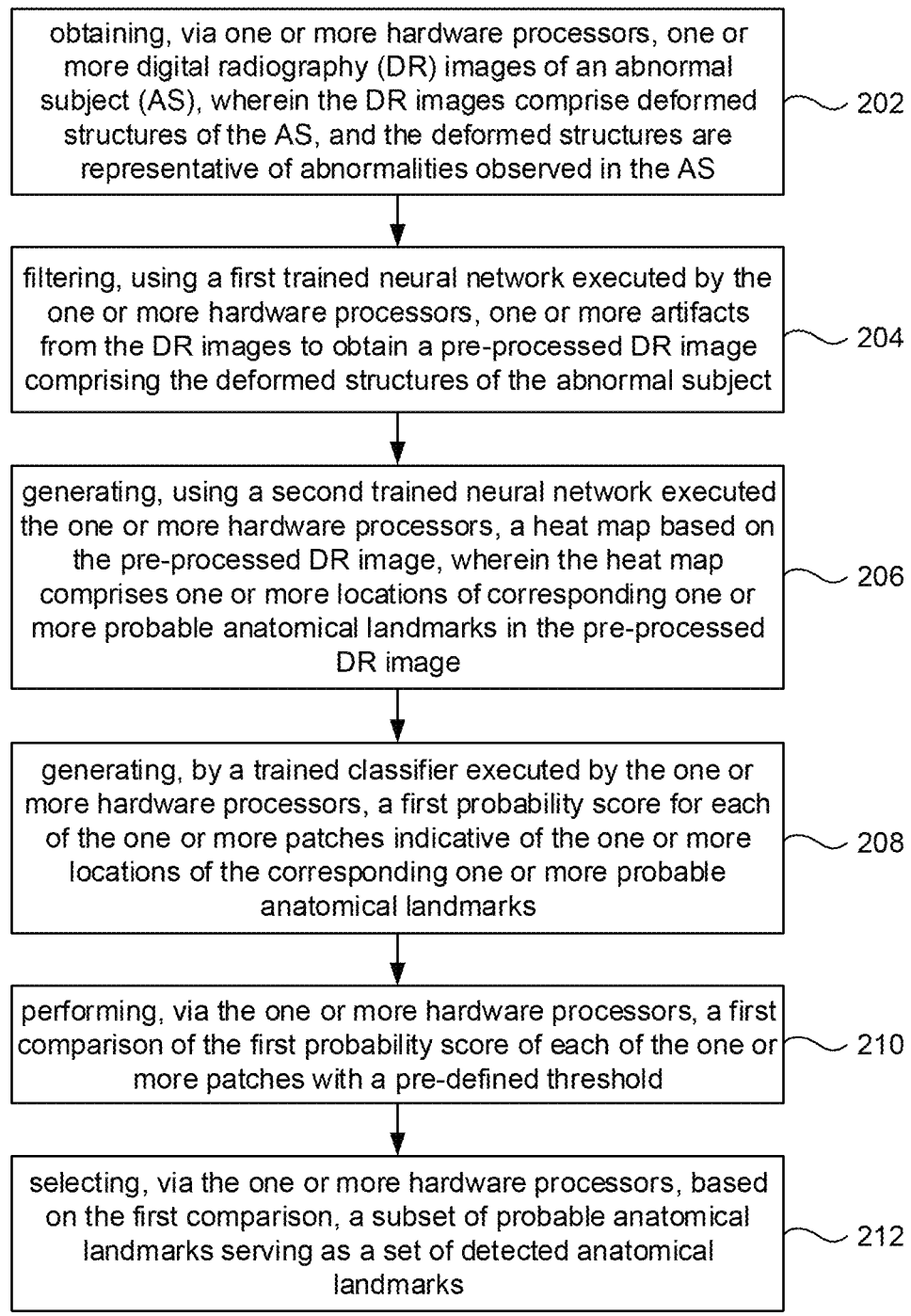
FIG. 2 depicts an exemplary flow chart illustrating a method for anatomical landmark detection and identification from digital radiography images containing severe skeletal deformations using the system of FIG. 1, in accordance with an embodiment of the present disclosure.

FIG. 2, with reference to FIG. 1, depicts an exemplary flow chart illustrating a method for anatomical landmark detection and identification from digital radiography images containing severe skeletal deformations using the system 100 of FIG. 1, in accordance with an embodiment of the present disclosure. In an embodiment, the system(s) 100 comprises one or more data storage devices or the memory 102 operatively coupled to the one or more hardware processors 104 and is configured to store instructions for execution of steps of the method by the one or more processors 104. The steps of the method of the present disclosure will now be explained with reference to components of the system 100 of FIG. 1, the flow diagram as depicted in FIG. 2 and diagrams of FIGS. 3-11B. In an embodiment, at step 202 of the present disclosure, the one or more hardware processors 104 obtain one or more digital radiography (DR) images of an abnormal subject. Each of the one or more DR images comprises one or more deformed structures (or deformations) of the abnormal subject wherein the one or more deformed structures are representative of one or more abnormalities observed in the abnormal subject. At step 204 of the present disclosure, the one or more hardware processors 104 filter, using a first trained neural network executed by the one or more hardware processors, one or more artifacts from the obtained one or more DR images to obtain a pre-processed DR image comprising the one or more deformed structures of the abnormal subject. In an embodiment, the expression 'pre-processed DR image' may also be referred as 'enhanced DR image' and may be interchangeably used herein.

Figure 3:
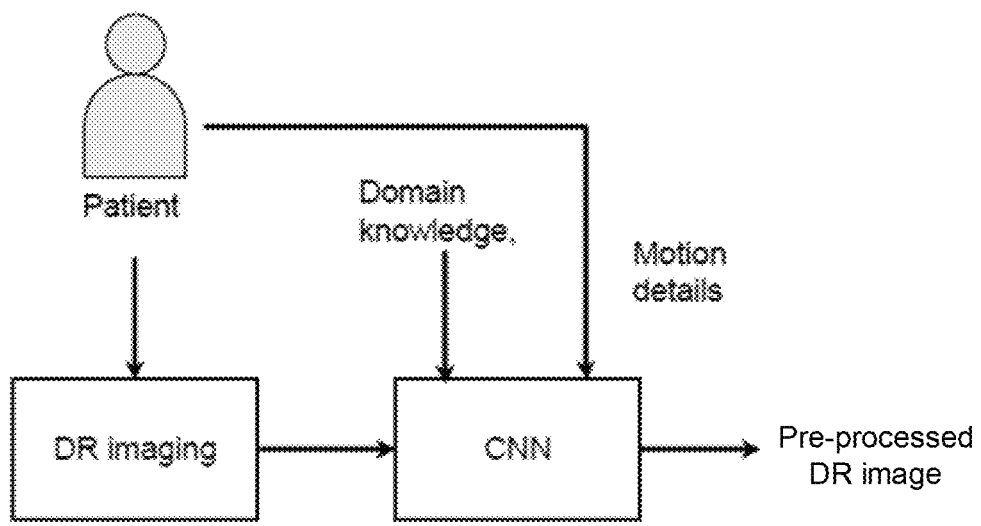
FIG. 3 depicts a first filtering technique applied on the one or more DR images obtained as an input by the system of FIG. 1, in accordance with an embodiment of the present disclosure.

In an embodiment, the pre-processed DR image is obtained by applying a 2-stage filtering technique. For instance, the first stage filtering technique comprises applying, by the first trained neural network, (i) the domain knowledge and (ii) motion details of the abnormal subject on the one or more DR images to obtain the pre-processed DR image. In an embodiment, the motion details during an exposure are captured through at least one of (i) one or more sensors attached to the abnormal subject and (ii) an external image capturing device such as a camera or a video recorder. FIG. 3, with reference to FIGS. 1-2, depicts a first filtering technique applied on the one or more DR images obtained as an input by the system 100 of FIG. 1, in accordance with an embodiment of the present disclosure. Motion artifacts observed while imaging different body parts may be different. Also, the artifacts observed depend on one or more angles in which the body part is being imaged. Another common cause of motion artefact is respiratory gating which can be divided into several phases. For robustness, the neural network of the system 100 as depicted in FIG. 3 is trained to handle different motions encountered. The motion details during the exposure are captured through either sensor attached to the abnormal subject/patient or through external cameras. During testing, appropriate network weights are chosen to obtain final image (e.g., pre-processed DR image).

Figure 4:
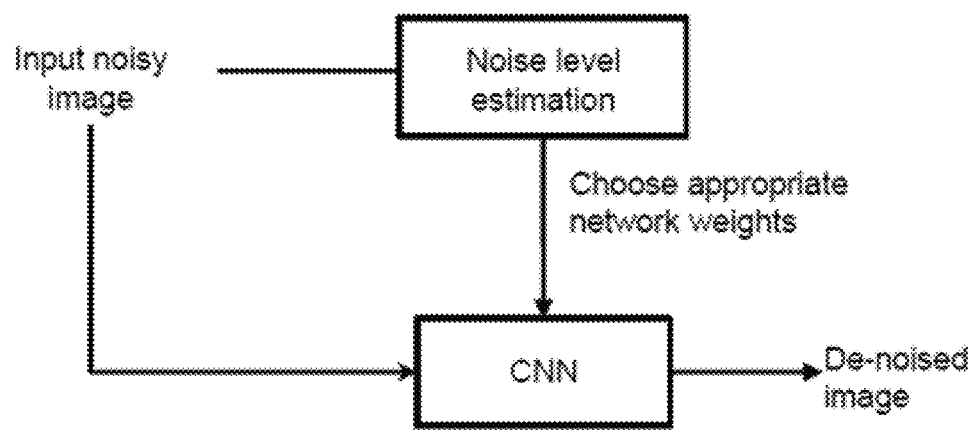
FIG. 4 depicts a second filtering technique applied either on an output of the first filtering technique or on the one or more DR images obtained as an input by the system of FIG. 1, in accordance with an embodiment of the present disclosure.

The second stage filtering technique comprises estimating a noise level in the obtained one or more DR images and applying one or more network weights of the first trained neural network to the obtained one or more DR images based on the estimated noise level to obtain the pre-processed DR image. FIG. 4, with reference to FIGS. 1 through 3, depicts a second filtering technique applied either on an output of the first filtering technique or on the one or more DR images obtained as an input by the system 100 of FIG. 1, in accordance with an embodiment of the present disclosure. For instance, if there is no requirement for motion artifacts removal then such filtering technique (e.g., the first filtering technique) may not be performed. Therefore, the obtained DR images can be directly fed to the system 100 for applying the second filtering technique to obtain the pre-processed DR image (also referred as 'denoised DR image' and may be interchangeably used herein). The underexposed/overexposed DR image may be corrupted by noise. Noise is generally characterized as Poisson. However, characterizing the noise exactly is difficult. In such a scenario it is best to use a neural network (e.g., a trained neural network such as a convolutional neural network (CNN), in one example embodiment) since it can learn the noise model from the data (DR images) itself. Since it is difficult to model the noise in this case, the trained neural network of FIG. 4 is implemented by the system 100 to de-noise the images. For robustness, the present disclosure implemented training for different CNNs to handle different noise levels. The first filtering technique and the second filtering technique may be applied by the system 100 based on the requirement and nature of the obtained DR images as input, so as to ensure that post correction of the motion artifacts and exposures, if any, the pre-processed DR image that is outputted is (i) free from one or more errors in the one or more artifacts and (ii) free from under exposure, (iii) free from over exposure, or (iv) combinations thereof.

Figure 5A:
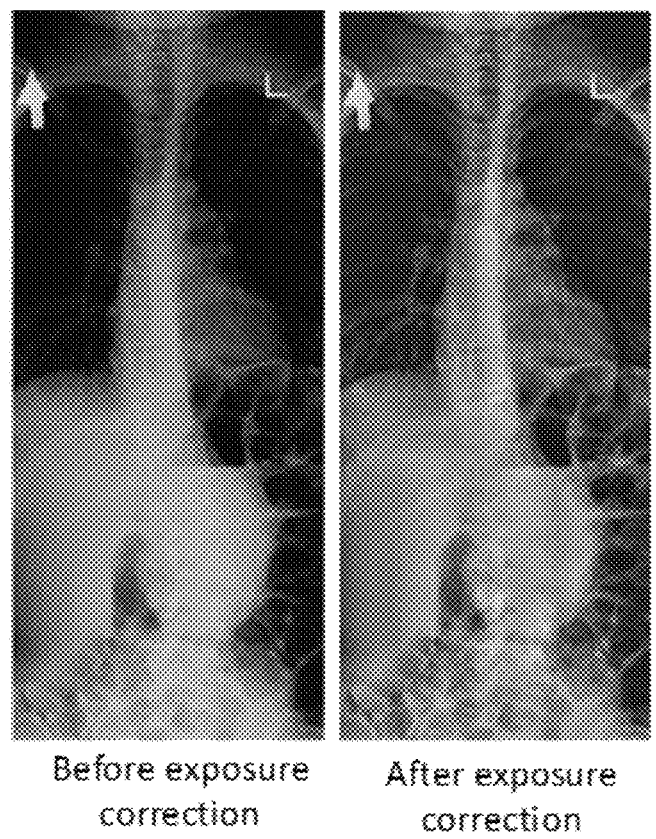
FIGS. 5A through 5C, illustrate a DR image that depicts before and after exposure correction, in accordance with an embodiment of the present disclosure.
Figure 5B:
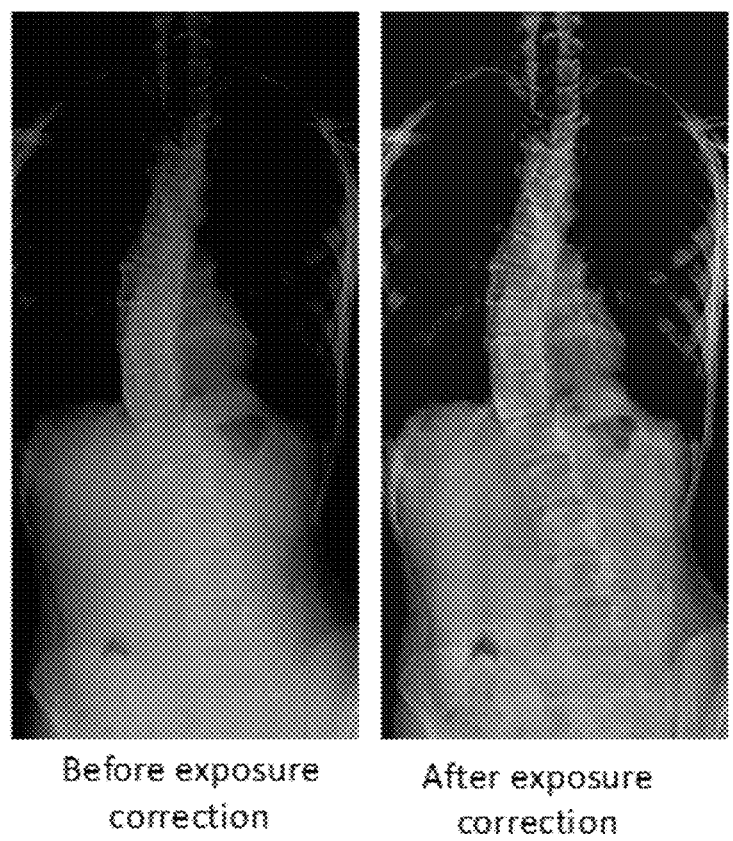
Figure 5C:
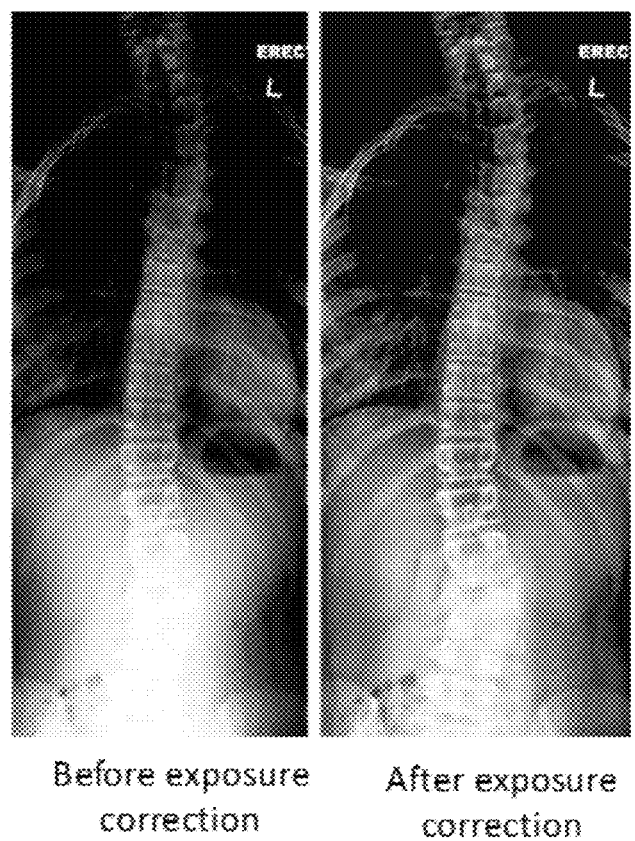

FIGS. 5A through 5C, illustrate a DR image that depicts before and after exposure correction, in accordance with an embodiment of the present disclosure. Images for processing exposure correction are obtained from a publicly available dataset. (e.g., refer to http://spineweb.digitalimaging-group.ca/spineweb/index.php?n=Main.Datasets and more specifically to "Dataset 16: 609 spinal anterior-posterior x-ray images"). Though there are no figures depicting removing of motion artefacts, it is to be understood by a person having ordinary skill in the art or person skilled in the art that outputs can be representatively provided but are refrained herein for the sake of brevity.

Figure 6A:
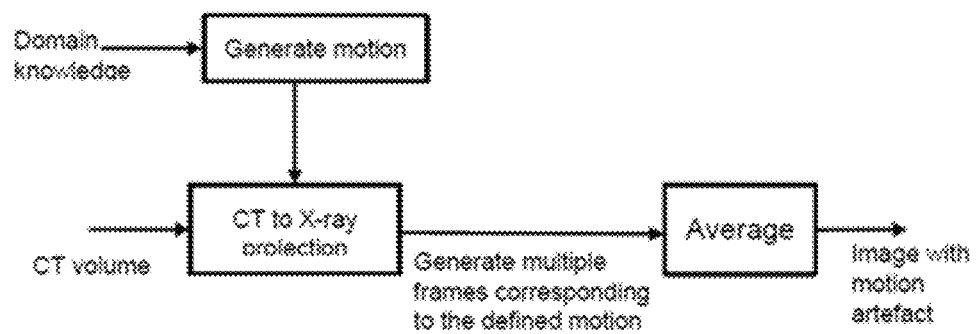
FIG. 6A depicts a block diagram illustrating a method for generating synthetic data comprising of images with artifacts, in accordance with an embodiment of the present disclosure.
Figure 6B:
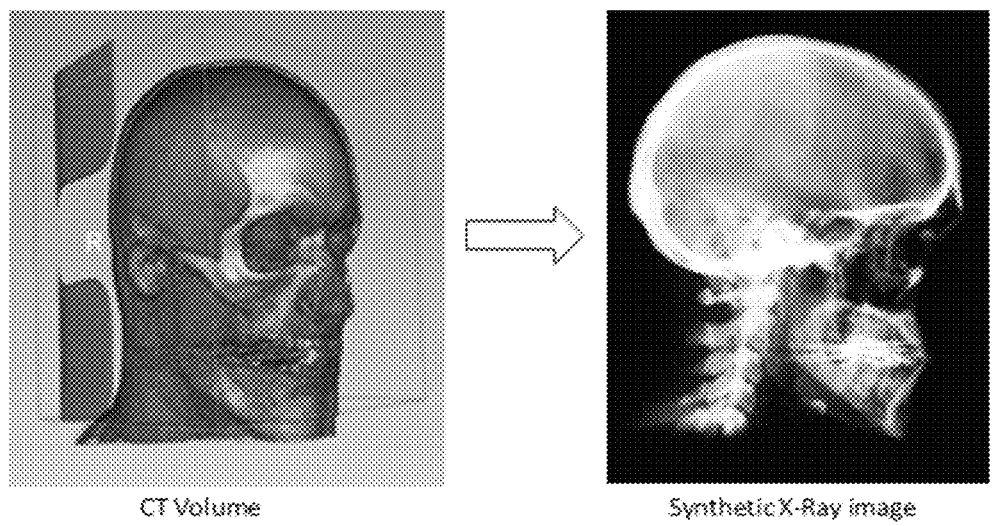
FIG. 6B depicts a representation of synthetic data generation from a computed tomography (CT) volume, in accordance with an example embodiment of the present disclosure.

At step 206 of the present disclosure, the one or more hardware processors 104 generate, using a second trained neural network executed the one or more hardware processors, a heat map based on the pre-processed DR image, wherein the heat map comprises one or more locations of corresponding one or more probable anatomical landmarks from the pre-processed DR image. The second trained neural network undergoes training via a large volume of DR images from which synthetic data can be generated. This synthetic data comprises of DR images and associated artefacts comprised in the DR images. As it can be realized that it is difficult to get a lot of data with artifacts for training a machine learning model such as a deep learning (DL) model/a neural network model. As a result, present disclosure has utilized large volume of CT volume data and artifacts were added to this to simulate the needed x-ray images with motion artifacts and exposure for training purposes. FIG. 6A, with reference to FIGS. 1 through 5C, depicts a block diagram illustrating a method for generating synthetic data comprising of images with artifacts, in accordance with an embodiment of the present disclosure. More specifically, the system 100 utilizes domain knowledge to generate motion artefacts which goes as an input along with CT images wherein CT image to (2D) x-ray projection is performed and multiple frames corresponding to defined motion(s) are generated. The multiple frames are then used for generating the synthetic data comprising of images with artifacts. More specifically, in the present disclosure, average of the multiple frames was taken for generating the synthetic data comprising of images with artifacts. It is to be understood by a person having ordinary skill in the art or person skilled in the art that any other operation may be carried on the multiple frames corresponding to defined motion(s) to generate the synthetic data. FIG. 6B, with reference to FIGS. 1 through 6A, depicts a representation of synthetic data generation from a CT volume, in accordance with an example embodiment of the present disclosure.

Once the synthetic data is generated, the system 100 uses this data comprising x-ray (DR) images with artefacts for training neural network(s). More specifically, the x-ray images with artefacts serve as a training dataset, in one example embodiment.

Figure 7A:
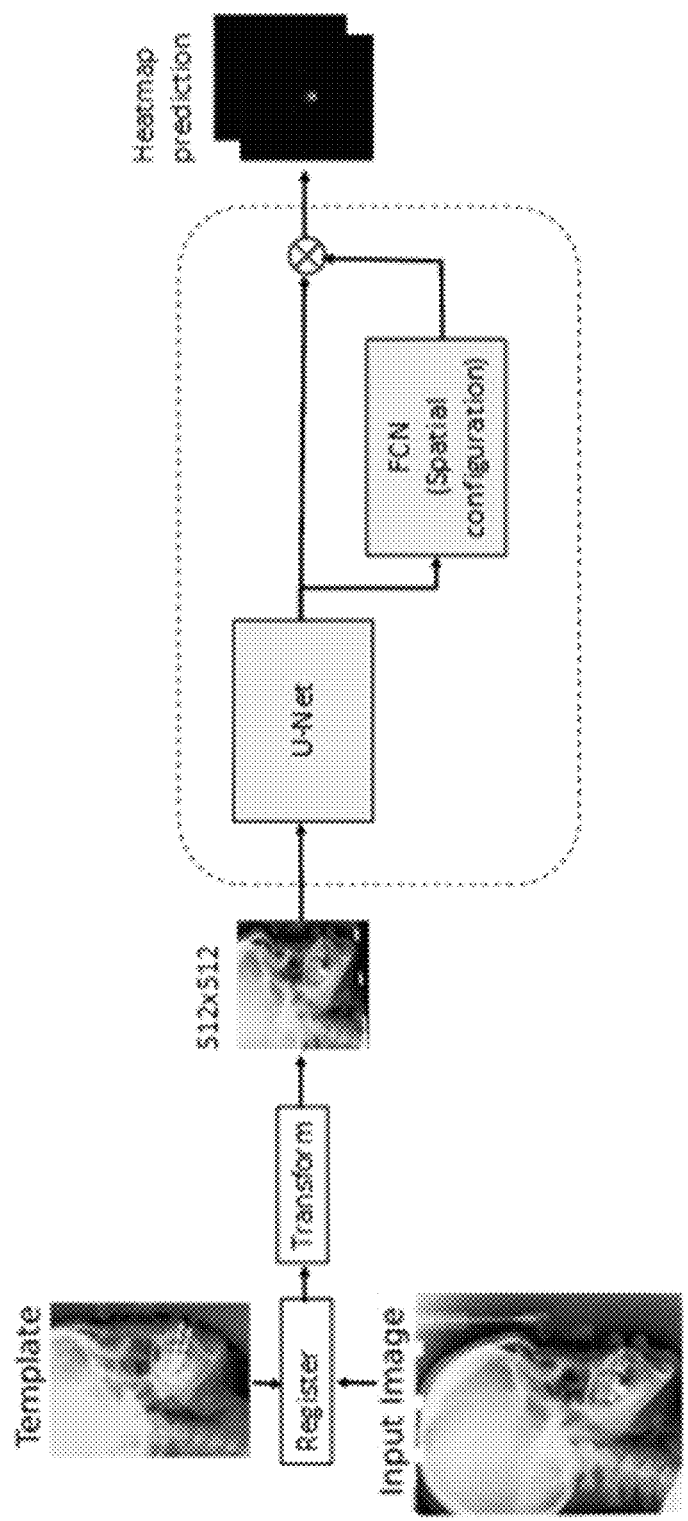
FIG. 7A depicts heat map prediction by a trained neural network of the system of FIG. 1, in accordance with an embodiment of the present disclosure.
Figure 7B:
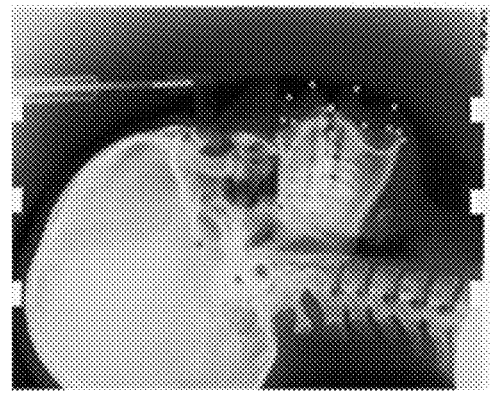
FIG. 7B depicts an exemplary representation of one or more probable landmarks identified by the trained neural network from a generated heat map for a given input DR image, in accordance with an embodiment of the present disclosure.
Figure 7B:
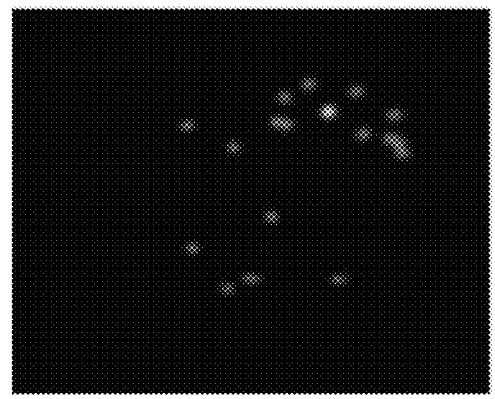
Figure 7B:
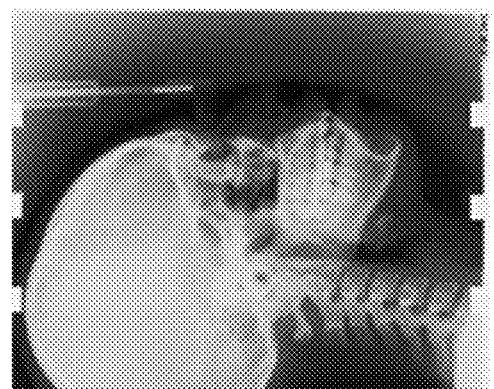

The one or more patches/one or more locations of the probable anatomical landmarks are depicted in a heat map generated as an output by the trained neural network. FIG. 7A, with reference to FIGS. 1 through 6B, depicts heat map prediction by the second trained neural network of the system 100 of FIG. 1, in accordance with an embodiment of the present disclosure. FIG. 7B, with reference to FIGS. 1 through 7A, depicts an exemplary representation of one or more probable landmarks identified by the second trained neural network from a generated heat map for a given input DR image, in accordance with an embodiment of the present disclosure. Images processed as inputs are depicted in FIGS. 6A through 7B by the system 100 to generate various outputs are obtained from publicly available datasets (e.g., refer https://www.kaggle.com/jiahonggian/cephalometric-landmarks).

Figure 8:
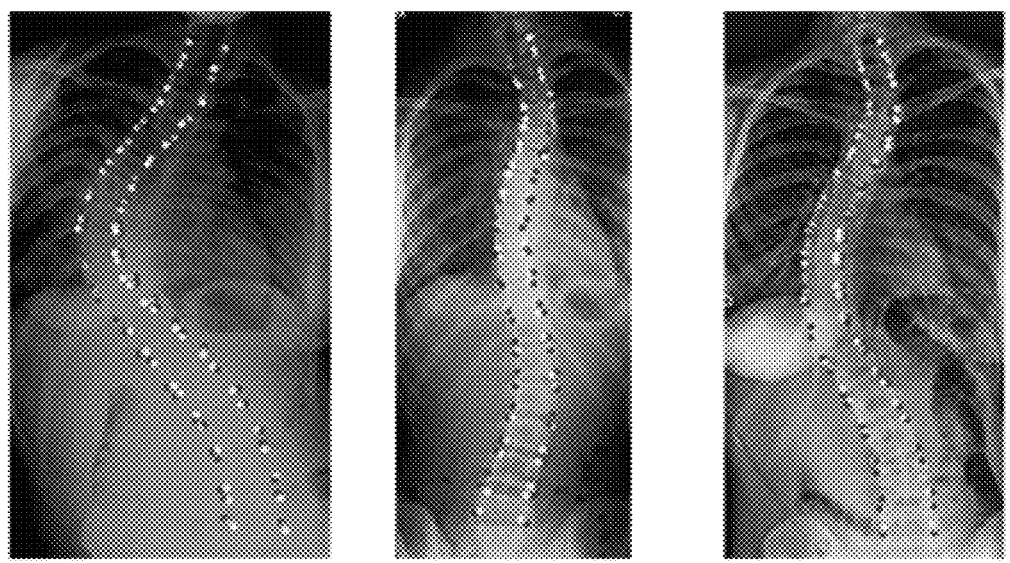
FIG. 8 depicts a representation of a subset of probable anatomical landmarks serving as a set of detected anatomical landmarks, in accordance with an embodiment of the present disclosure.

Upon obtaining the one or more probable anatomical landmarks, at step 208 of the present disclosure, the one or more hardware processors 105 generate, by using a trained classifier, a first probability score for each of the one or more locations of the corresponding one or more probable anatomical landmarks. In other words, the heat map includes the one or more probable anatomical landmarks, wherein the trained classifier assigns a score for each of the one or more probable anatomical landmarks. Example of the trained classifier may conclude but not limited to random forest classifier, support vector machine and the like. At step 210 of the present disclosure, the one or more hardware processors 104 perform a first comparison of the first probability score of each of the one or more patches with a pre-defined threshold. The threshold may also be empirically determined depending upon (i) the one or more probable anatomical landmarks identified and/or (ii) obtained DR images as input, in one example embodiment. The threshold may also be empirically determined based on the level of training of the system 100 (e.g., including the training of neural networks comprised in the system 100), in another example embodiment. At step 212 of the present disclosure, based on the first comparison, the one or more hardware processors 104 select a subset of probable anatomical landmarks serving as a set of detected anatomical landmarks. In other words, at least a subset of probable anatomical landmarks from the one or more probable anatomical landmarks are identified as accurate anatomical landmarks from the pre-processed DR image. FIG. 8, with reference to FIGS. 1 through 7B, depicts a representation of the subset of probable anatomical landmarks serving as the set of detected anatomical landmarks, in accordance with an embodiment of the present disclosure. More specifically, black/grey dot are the anatomical landmarks detected by the system 100 using the trained classifier, in one example embodiment. The white dot depicting a set of anatomical landmarks are landmarks annotated by a subject matter expert (e.g., a medical professional).

Figure 9:
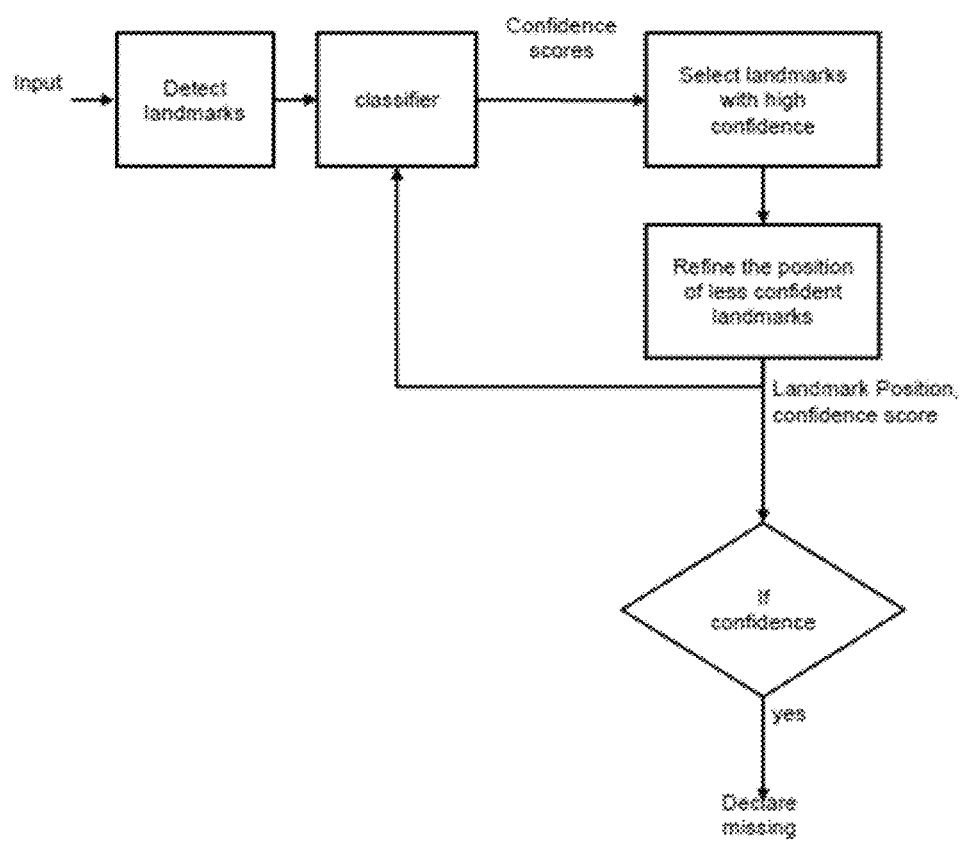
FIG. 9 depicts a block diagram illustrating a method for accurate anatomical landmarks detection from a pre-processed DR image using the trained classifier implemented by the system of FIG. 1, in accordance with an embodiment of the present disclosure.

FIG. 9, with reference to FIGS. 1 through 8, depicts a block diagram illustrating a method for accurate anatomical landmarks detection from the pre-processed DR image using the trained classifier implemented by the system 100 of FIG. 1, in accordance with an embodiment of the present disclosure. In an embodiment, each detected anatomical landmark from the set of detected anatomical landmarks has the first probability score higher than the pre-defined threshold. The identification of probable anatomical landmarks as one of the accurate anatomical landmark or the missing anatomical landmark is/may be an iterative process.

The remaining probable anatomical landmarks having score less than the pre-defined threshold are fine-tuned and these remaining fine-tune landmarks from the set of fine-tuned probable anatomical landmarks further go for another iteration of classification For instance, the trained classifier generates a second probability score for the set of fine-tuned probable anatomical landmarks and a second comparison is performed between the second probability score of each fine-tuned probable anatomical landmark from the set of fine-tuned probable anatomical landmarks with the pre-defined threshold. Based on the second comparison, a subset of probable anatomical landmarks serving as another set of detected anatomical landmarks are identified or these are classified as missing anatomical landmarks. In other words, the remaining fine-tuned probable anatomical landmarks after which a score is assigned if determined that the score is still less than the pre-defined threshold, then these remaining fine-tuned probable anatomical landmarks from the set of fine-tuned probable anatomical landmarks can be identified as the missing anatomical landmarks.

Figure 10:
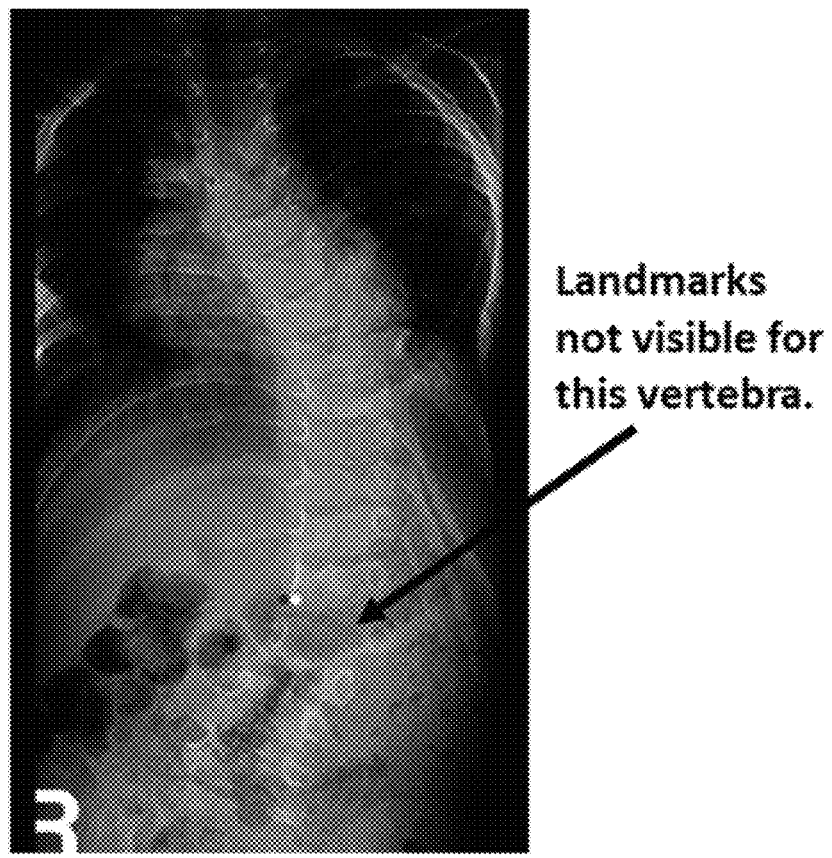
FIG. 10 depicts a representation of a DR image indicative of a missing anatomical prediction, in accordance with an embodiment of the present disclosure.

The above iterative process of anatomical landmarks detection using the trained classifier can be better understood by way of following example: For instance, say, there are 10 probable anatomical landmarks for which a score is generated by the trained classifier (e.g., the classifier is comprised in the memory 102 of the system 100). Each of the score of the 10 probable anatomical landmarks are compared with the pre-defined threshold. Let the pre-defined threshold be 0.9. Based on the comparison, say first 6 probable anatomical landmarks are identified as the accurate anatomical landmarks as their score is higher than the pre-defined threshold. The remaining 4 probable anatomical landmarks may not be selected since their score may be less than the pre-defined threshold. Therefore, the remaining 4 probable anatomical landmarks may be further fine-tuned (refining the position of these landmarks using the anatomical atlas comprised in the memory 102 to obtain a set of fine-tuned probable anatomical landmarks, in one example embodiment. The remaining 4 probable anatomical landmarks may not be fine-tuned and be further classified as missing anatomical landmarks, in another example embodiment. In case the remaining 4 probable anatomical landmarks are fine-tuned, the fine-tuned probable anatomical landmarks are once again fed to the trained classifier and a score is generated for each of the fine-tuned probable anatomical landmarks. This score is once again compared with the pre-defined threshold and based on the comparison, the remaining 4 probable anatomical landmarks or at least a subset of the remaining 4 probable anatomical landmarks may be identified as one of accurate anatomical landmark or a missing anatomical landmark. FIG. 10, with reference to FIGS. 1 through 9, depicts a representation of a DR image indicative of a missing anatomical prediction, in accordance with an embodiment of the present disclosure.

If there are any anatomical landmarks from the one or more probable anatomical landmarks that are misaligned or remain undiscovered in step 206, then these misaligned are corrected by a generated deformable model by utilizing the (i) an anatomical atlas comprised in the memory 102, and (ii) an associated domain knowledge comprised in the memory 102 to obtain one or more accurate anatomical landmarks. In other words, the system 100 determines if any of the one or more probable anatomical landmarks identified in step 206 are misaligned. Based on the determination, the system 100 realigns the misaligned anatomical landmarks to a desired position. To perform realigning of the misaligned landmarks, a three-dimensional (3D) deformable model may be generated using 3D CT voxel data wherein one or more deformations are applied, and the generated 3D deformable model is then converted to a 2D image (also referred as three-dimensional (3D) based two-dimensional (2D) deformable model or 3D based 3D image). The 3D based 2D deformable model may also be referred as '3D deformable model projected onto 2D image' and may be interchangeably used herein, in one example embodiment of the present disclosure. The 3D based 2D deformable model/3D based 3D image is compared with the input DR image to determine similarities and/or to check if these are identical. Based on the comparison of the 3D based 2D deformable model with the input DR image, one or more atlas deformed landmarks may be obtained as output. The one or more atlas deformed anatomical landmarks are compared with the one or more probable anatomical landmarks of step 206 by utilizing the domain knowledge to determine if any of the probable anatomical landmarks are misaligned. The misaligned anatomical landmarks may be realigned from a current position to a desired position. In an embodiment, there could be scenarios where post refinement/realignment, the position of misaligned anatomical landmarks (now realigned) may not change, and such landmarks may be classified as a missing landmark. For instance, there are 10 probable anatomical landmarks of which 6 were declared as accurate anatomical landmarks in step 212. The remaining 4 probable anatomical landmarks were processed for realignment. The output of realignment can either result in zero number of accurate anatomical landmarks where all the 4 can be identified as missing anatomical landmark, in one example embodiment. Alternatively, 'x' number of the remaining 4 probable anatomical landmark post realignment can be identified as an accurate anatomical landmark(s), wherein 'x' may take a value between 1 and 4, in another example embodiment.

Figure 11A:
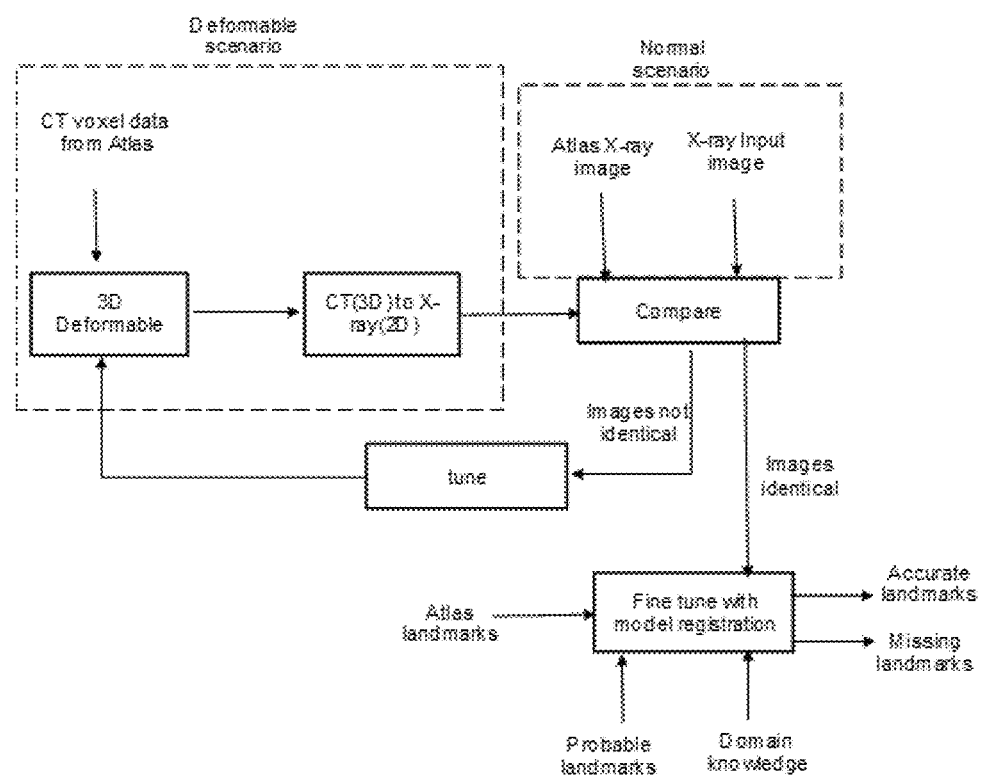
FIG. 11A depicts a block diagram illustrating a method for realigning one or more misaligned anatomical landmarks identified from the one or more probable anatomical landmarks and identifying the one or more realigned anatomical landmarks as at least one of a set of accurate anatomical landmarks and a set of missing anatomical landmarks by the system of FIG. 1, in accordance with an embodiment of the present disclosure.

FIG. 11A, with reference to FIG. 10, depicts a block diagram illustrating a method for realigning one or more misaligned anatomical landmarks identified from the one or more probable anatomical landmarks and identifying the one or more realigned anatomical landmarks as at least one of a set of accurate anatomical landmarks and a set of missing anatomical landmarks by the system 100 of FIG. 1, in accordance with an embodiment of the present disclosure. More specifically, FIG. 11A depicts a block diagram illustrating a method for determining one or more misaligned anatomical landmarks in the one or more probable anatomical landmarks and realigning the determined one or more misaligned anatomical landmarks to a desired position, in accordance with an embodiment of the present disclosure. The one or more misaligned anatomical landmarks are realigned to a desired position by the pre-generated deformable model by utilizing at least one of an anatomical atlas and an associated domain knowledge comprised in the memory 102.

Figure 11B:
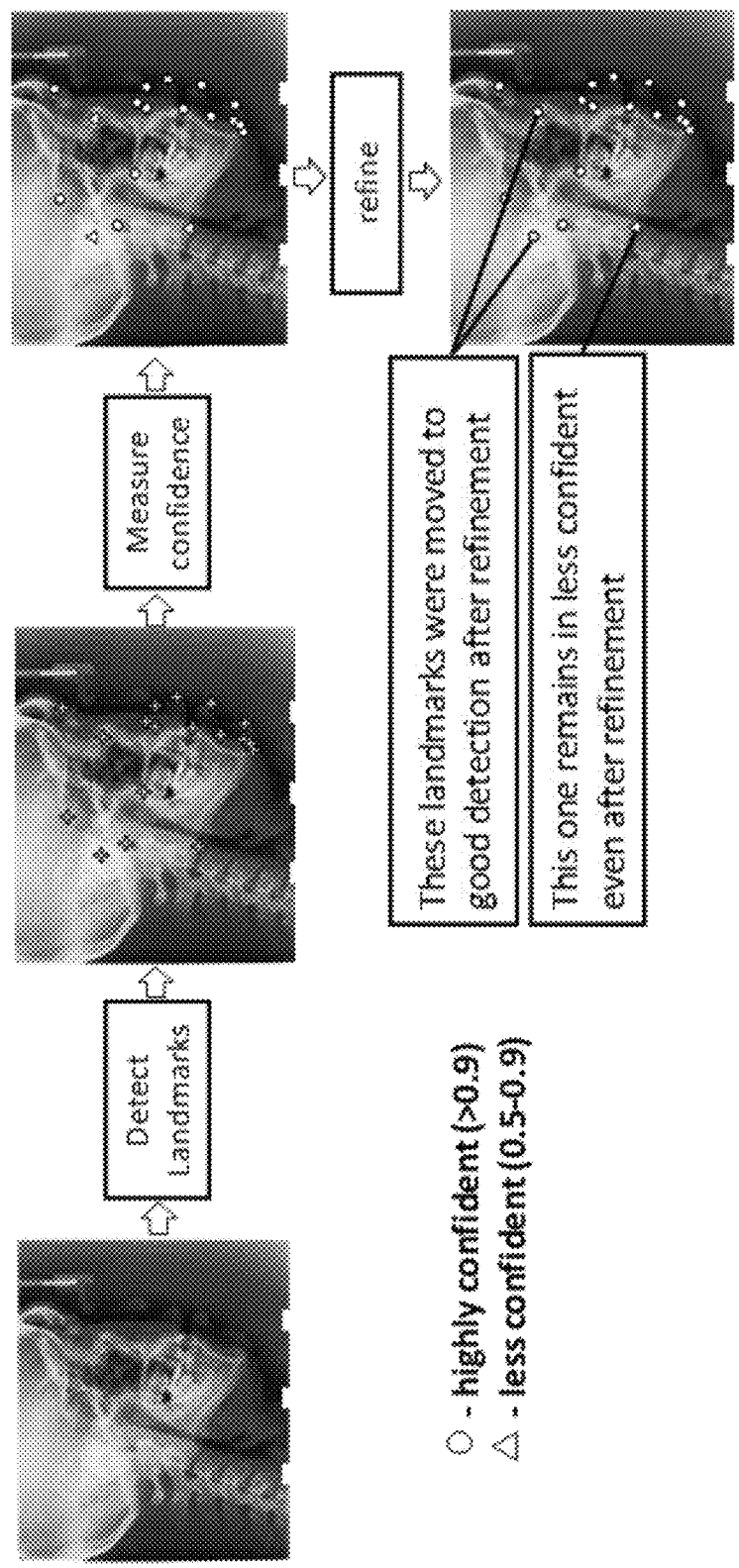
FIG. 11B depicts a pictorial representation of the realignment method of FIG. 11A being performed on an input DR image having the one or more misaligned anatomical landmarks identified from the one or more probable anatomical landmarks to obtain at least one of a set of accurate anatomical landmarks and a set of missing anatomical landmarks, in accordance with an embodiment of the present disclosure.

FIG. 11B depicts a pictorial representation of the realignment method of FIG. 11 being performed on an input DR image having the one or more misaligned anatomical landmarks identified from the one or more probable anatomical landmarks to obtain at least one of a set of accurate anatomical landmarks and a set of missing anatomical landmarks, in accordance with an embodiment of the present disclosure.

It is to be understood by a person having ordinary skill in the art or person skilled in the art that though the present disclosure describes a system and method for anatomical landmark detection and identification from digital radiography images containing severe skeletal deformations, there could be scenarios where the system 100 may receive an input x-ray image of a normal subject wherein no skeletal deformations are observed. In such scenarios, the generated probable anatomical landmarks are registered and compared with atlas image landmarks and domain knowledge for error prediction and correction as applicable.

Embodiments of the present disclosure provide systems and methods for detecting anatomical landmarks in challenging situations where there are artifacts. Detecting landmark accurately in a clear image by itself is very complicated and with the presence of anomalies such as motion artifacts, exposure variations it becomes even more difficult and challenging. Method of the present disclosure enables identification of accurate anatomical landmarks that increase the accuracy of automatic detection and reduces the patient of being further exposed by eliminating these artifacts from the images. The system of the present disclosure enables detection of meaningful information rather than subject the patient to another scan. The present disclosure can also be implemented in certain disorders such as Parkinson's and anxiety disorders which makes it difficult to keep the patient steady. Other applications where the present disclosure and its systems and methods can be implemented include, but are not limited to, automated digital templating to identify right implant sizes in knee and hip surgeries, pre-surgery planning to ensure key anatomical areas are not touched during surgery and eliminates the need by expert to manually identify landmarks from images as the process is automated with elimination of inter observer variations and errors. It is to be understood by person having ordinary skill in the art and/or person skilled in the art that examples of Cephalometric (skull related figures) and Scoliosis (spine related figures) shall not be construed as limiting the scope of the present disclosure and the systems and methods of the present disclosure can be implemented for detection of accurate anatomical landmarks from any body parts of subjects/human beings. Likewise, the realignment of misaligned anatomical landmarks can be performed basis identification of misaligned anatomical landmarks from the probable anatomical landmarks.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor implemented method for detecting anatomical landmarks in abnormal subjects, the processor implemented method comprising:
   obtaining, via one or more hardware processors, one or more digital radiography (DR) images of an abnormal subject, wherein the one or more DR images comprise one or more deformed structures of the abnormal subject, and wherein the one or more deformed structures are representative of one or more abnormalities observed in the abnormal subject;

filtering, using a first trained neural network executed by the one or more hardware processors, one or more artifacts from the obtained one or more DR images to obtain a pre-processed DR image comprising the one or more deformed structures of the abnormal subject;

generating, using a second trained neural network executed by the one or more hardware processors, a heat map based on the pre-processed DR image, wherein the heat map comprises one or more locations of corresponding one or more probable anatomical landmarks in the pre-processed DR image;

generating, by a trained classifier executed by the one or more hardware processors, a first probability score for each of the one or more locations of the corresponding one or more probable anatomical landmarks in the pre-processed DR image;

performing, via the one or more hardware processors, a first comparison of the first probability score for each of the one or more locations of the corresponding one or more probable anatomical landmarks in the pre-processed DR image with a pre-defined threshold; and selecting, via the one or more hardware processors, based on the first comparison, a subset of the corresponding one or more probable anatomical landmarks in the pre-processed DR image serving as a set of detected anatomical landmarks.

2. The processor implemented method as claimed in claim 1, wherein each detected anatomical landmark from the set of detected anatomical landmarks has the first probability score higher than the pre-defined threshold.

3. The processor implemented method as claimed in claim 1, wherein for a remaining subset of probable anatomical landmarks from the one or more probable anatomical landmarks having the first probability score less than the pre-defined threshold, the processor implemented method further comprises:

fine-tuning the remaining subset of probable anatomical landmarks from the one or more probable anatomical, landmarks by using an anatomical atlas stored in a memory to obtain a set of fine-tuned probable anatomical landmarks; or identifying the remaining subset of probable anatomical landmarks from the one or more probable anatomical landmarks as one or more missing anatomical landmarks.

4. The processor implemented method as claimed in claim 3, further comprising:

generating, by the trained classifier, a second probability score for the set of fine-tuned probable anatomical landmarks;

performing a second comparison of the second probability score of each fine-tuned probable anatomical landmark from the set of fine-tuned probable anatomical landmarks with the pre-defined threshold; and selecting, based on the second comparison, a subset of probable anatomical landmarks serving as another set of detected anatomical landmarks.

5. The processor implemented method as claimed in claim 4, further comprising: identifying remaining fine-tuned probable anatomical landmarks from the set of fine-tuned probable anatomical landmarks as one or more missing anatomical landmarks, wherein each of the one or more identified missing anatomical landmarks has the second probability score less than the pre-defined threshold.

6. The processor implemented method as claimed in claim 1, wherein the step of filtering, using a first trained neural network, one or more artifacts from the obtained one or more DR images to obtain a pre-processed DR image comprises:

(a) applying, by the first trained neural network, (i) domain knowledge and (ii) motion details of the abnormal subject on the one or more DR images to obtain the pre-processed DR image, wherein the motion details of the abnormal subject during an exposure are captured through at least one of (i) one or more sensors attached to the abnormal subject and (ii) an external image capturing device; and (b) estimating a noise level in the obtained one or more DR images, and applying one or more network weights of the first trained neural network to the obtained one or more DR images based on the estimated noise level to obtain the pre-processed DR image.

7. The processor implemented method as claimed in claim 1, further comprising:

determining one or more misaligned anatomical landmarks from the one or more probable anatomical landmarks;

realigning, by using a three-dimensional (3D) based two-dimensional (2D) deformable model, the one or more misaligned anatomical landmarks to a desired position by using at least one of an anatomical atlas and an associated domain knowledge stored in a memory, to obtain one or more realigned anatomical landmarks; and identifying the one or more realigned anatomical landmarks as a set of accurate anatomical landmarks or a set of missing anatomical landmarks.

8. A system for detecting anatomical landmarks in abnormal subjects, the system comprising:

a memory storing instructions;

one or more communication interfaces; and one or more hardware processors coupled to the memory via the one or more communication interfaces, wherein the one or more hardware processors are configured by the instructions to:

obtain one or more digital radiography (DR) images of an abnormal subject, wherein the one or more DR images comprise one or more deformed structures of the abnormal subject, and wherein the one or more deformed structures are representative of one or more abnormalities observed in the abnormal subject;

filter, using a first trained neural network executed by the one or more hardware processors, one or more artifacts from the obtained one or more DR images to obtain a pre-processed DR image comprising the one or more deformed structures of the abnormal subject;

generate, using a second trained neural network executed by the one or more hardware processors, a heat map based on the pre-processed DR image, wherein the heat map comprises one or more locations of corresponding one or more probable anatomical landmarks in the pre-processed DR image;

generate, by a trained classifier executed by the one or more hardware processors, a first probability score for each of the one or more locations of the corresponding one or more probable anatomical landmarks in the pre-processed DR image;

perform a first comparison of the first probability score for each of the one or more locations of the corresponding one or more probable anatomical landmarks in the pre-processed DR image with a pre-defined threshold; and select, based on the first comparison, a subset of the corresponding one or more probable anatomical landmarks in the pre-processed DR image serving as a set of detected anatomical landmarks.

9. The system as claimed in claim 8, wherein each detected anatomical landmark from the set of detected anatomical landmarks has the first probability score higher than the pre-defined threshold.

10. The system as claimed in claim 8, wherein for a remaining subset of probable anatomical landmarks from the one or more probable anatomical landmarks having the first probability score less than the pre-defined threshold, the one or more hardware processors are further configured to:

fine-tune the remaining subset of probable anatomical landmarks from the one or more probable anatomical landmarks by using an anatomical atlas stored in the memory to obtain a set of fine-tuned probable anatomical landmarks; or identify the remaining subset of probable anatomical landmarks from the one or more probable anatomical landmarks as one or more missing anatomical landmarks.

11. The system as claimed in claim 10, wherein the one or more hardware processors are further configured to:

generate, by using the trained classifier, a second probability score for the set of fine-tuned probable anatomical landmarks;

perform a second comparison of the second probability score of each fine-tuned probable anatomical landmark from the set of fine-tuned probable anatomical landmarks with the pre-defined threshold; and select, based on the second comparison, a subset of probable anatomical landmarks serving as another set of detected anatomical landmarks.

12. The system as claimed in claim 11, wherein the one or more hardware processors are further configured to: identify remaining fine-tuned probable anatomical landmarks from the set of fine-tuned probable anatomical landmarks as one or more missing anatomical landmarks, wherein each of the one or more identified missing anatomical landmarks has the second probability score less than the pre-defined threshold.

13. The system as claimed in claim 8, further comprising: at least one of:
(i) one or more sensors attached to the abnormal subject, and
(ii) an external image capturing device for capturing motion details of the one or more abnormal subjects, and wherein the one or more sensors or the external image capturing device captures the motion details of the abnormal subject during an exposure, and
wherein the one or more artifacts from the obtained one or more DR images are filtered to obtain the pre-processed DR image by:
(a) applying, by the first trained neural network, (i) domain knowledge and (ii) the motion details of the abnormal subject on the one or more DR images to obtain the pre-processed DR image, and
(b) estimating a noise level in the obtained one or more DR images, and applying one or more network weights of the first trained neural network to the obtained one or more DR images based on the estimated noise level to obtain the pre-processed DR image.

14. The system as claimed in claim 8, wherein the one or more hardware processors are further configured to:

determine one or more misaligned anatomical landmarks from the one or more probable anatomical landmarks;

realign, by using a three-dimensional (3D) based two-dimensional (2D) deformable model, the one or more misaligned anatomical landmarks to a desired position by using at least one of an anatomical atlas and an associated domain knowledge stored in the memory, to obtain one or more realigned anatomical landmarks; and identify the one or more realigned anatomical landmarks as a set of accurate anatomical landmarks or a set of missing anatomical landmarks.

15. A computer program product comprising a non-transitory computer readable medium having a computer readable program embodied therein, wherein the computer readable program, when executed by one or more hardware processors, causes the one or more hardware processors to detect anatomical landmarks in abnormal subjects by:

obtaining, via one or more hardware processors, one or more digital radiography (DR) images of an abnormal subject, wherein the one or more DR images comprise one or more deformed structures of the abnormal subject, and wherein the one or more deformed structures are representative of one or more abnormalities observed in the abnormal subject;

filtering, using a first trained neural network executed by the one or more hardware processors, one or more artifacts from the obtained one or more DR images to obtain a pre-processed DR image comprising the one or more deformed structures of the abnormal subject;

generating, using a second trained neural network executed by the one or more hardware processors, a heat map based on the pre-processed DR image, wherein the heat map comprises one or more locations of corresponding one or more probable anatomical landmarks in the pre-processed DR image;

generating, by a trained classifier executed by the one or more hardware processors, a first probability score for each of the one or more locations of the corresponding one or more probable anatomical landmarks;

performing, via the one or more hardware processors, a first comparison of the first probability score of each of the one or more locations with a pre-defined threshold; and selecting, via the one or more hardware processors, based on the first comparison, a subset of the corresponding one or more probable anatomical landmarks serving as a set of detected anatomical landmarks.

16. The computer program product as claimed in claim 15, wherein each detected anatomical landmark from the set of detected anatomical landmarks has the first probability score higher than the pre-defined threshold.

17. The computer program product as claimed in claim 15, wherein for a remaining subset of probable anatomical landmarks from the one or more probable anatomical landmarks having the first probability score less than the pre-defined threshold, the computer readable program when executed by the one or more hardware processors further causes:

fine-tuning the remaining subset of probable anatomical landmarks from the one or more probable anatomical landmarks by using an anatomical atlas stored in a memory to obtain a set of fine-tuned probable anatomical landmarks; or identifying the remaining subset of probable anatomical landmarks from the one or more probable anatomical landmarks as one or more missing anatomical landmarks.

18. The computer program product as claimed in claim 17, wherein the computer readable program when executed by the one or more hardware processors further causes:
  generating, by the trained classifier, a second probability score for the set of fine-tuned probable anatomical landmarks;
  performing a second comparison of the second probability score of each fine-tuned probable anatomical landmark from the set of fine-tuned probable anatomical landmarks with the pre-defined threshold; and
  selecting, based on the second comparison, a subset of probable anatomical landmarks serving as another set of detected anatomical landmarks.

19. The computer program product as claimed in claim 18, wherein the computer readable program when executed by the one or more hardware processors further causes: identifying remaining fine-tuned probable anatomical landmarks from the set of fine-tuned probable anatomical landmarks as one or more missing anatomical landmarks, wherein each of the one or more identified missing anatomical landmarks has the second probability score less than the pre-defined threshold.

20. The computer program product as claimed in claim 15, wherein the computer readable program when executed by the one or more hardware processors further causes:
  determining one or more misaligned anatomical landmarks from the one or more probable anatomical landmarks;
  realigning, by using a three-dimensional (3D) based two-dimensional (2D) deformable model, the one or more misaligned anatomical landmarks to a desired position by using at least one of an anatomical atlas and an associated domain knowledge stored in a memory, to obtain one or more realigned anatomical landmarks; and
  identifying the one or more realigned anatomical landmarks as a set of accurate anatomical landmarks or a set of missing anatomical landmarks.

* * * * *